(12) United States Patent
Furuta et al.

(10) Patent No.: US 7,723,439 B2
(45) Date of Patent: May 25, 2010

(54) PROCESS FOR PRODUCING A POLYFLUOROALKYL (METH)ACRYLATE

(75) Inventors: Shoji Furuta, Kanagawa (JP); Taiki Hoshino, Kanagawa (JP); Ryuji Seki, Kanagawa (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 12/350,502

(22) Filed: Jan. 8, 2009

(65) Prior Publication Data

US 2009/0118433 A1 May 7, 2009

Related U.S. Application Data

(63) Continuation of application No. 10/859,213, filed on Jun. 3, 2004.

(30) Foreign Application Priority Data

Jun. 5, 2003 (JP) .............................. 2003-160885

(51) Int. Cl.
*C08L 27/22* (2006.01)
*C08F 114/18* (2006.01)

(52) U.S. Cl. .............. 525/330.4; 525/330.5; 525/330.3; 526/242

(58) Field of Classification Search .............. 525/330.4, 525/330.5, 330.3; 526/242
See application file for complete search history.

(56) References Cited

U.S. PATENT DOCUMENTS 3,239,557 A 3/1966 Fasick 6,409,886 B1 6/2002 Matsumoto et al.

FOREIGN PATENT DOCUMENTS

| EP | 1 195 370 | | 4/2002 |
|---|---|---|---|
| EP | 1 195 370 A1 | * | 4/2002 |
| EP | 1 364 934 | | 11/2003 |
| JP | 39-18112 | | 8/1964 |
| JP | 2000-355570 | | 12/2000 |
| JP | 2001-19663 | | 1/2001 |

OTHER PUBLICATIONS

The Fourth Series of Experimental Chemistry 1, Basic operation, Japan, Maruzen Co., Ltd., Nov. 5, 1990, pp. 214-226.
The Fourth Series of Experimental Chemistry 1, Basic operation, Japan, Maruzen Co., Ltd., Nov. 5, 1990, pp. 190-191.

* cited by examiner

*Primary Examiner*—Robert D. Harlan
(74) *Attorney, Agent, or Firm*—Oblon, Spivak, McClelland, Maier & Neustadt, L.L.P.

(57) ABSTRACT

A process for producing a polyfluoroalkyl (meth)acrylate, which comprises isolating, from a reaction mixture containing a polyfluoroalkyl (meth)acrylate obtained by reacting a polyfluoroalkyl iodide of the formula $C_nF_{2n+1}(CH_2)_mI$ (wherein n is an integer of from 2 to 7, and m is an integer of from 1 to 4) with a metal (meth)acrylate in tert-butanol, said polyfluoroalkyl (meth)acrylate by the following steps (1) to (3):

(1) a step of taking out a crude liquid from the reaction mixture by solid-liquid separation;
(2) a step of distilling the crude liquid to separate it into compound group A of compounds having a lower boiling point than the polyfluoroalkyl (meth)acrylate and compound group B of the polyfluoroalkyl (meth)acrylate and compounds having a higher boiling point than the polyfluoroalkyl (meth)acrylate; and
(3) a step of distilling and purifying the polyfluoroalkyl (meth)acrylate from the compound group B in the presence of a polymerization inhibitor.

19 Claims, 2 Drawing Sheets

PROCESS FOR PRODUCING A POLYFLUOROALKYL (METH)ACRYLATE

This is a continuation application of U.S. application Ser. No. 10/859,213, filed Jun. 3, 2004.

The present invention relates to a process for producing a polyfluoroalkyl (meth)acrylate.

A fluorinated copolymer obtained by copolymerizing a polyfluoroalkyl (meth)acrylate (hereinafter referred to also as a fluorinated compound) with a monomer polymerizable with a fluorinated compound, is useful as a raw material for a water and oil repellent for fibers. In this specification, a polyfluoroalkyl acrylate and a polyfluoroalkyl (meth)acrylate will be generally referred to as a polyfluoroalkyl (meth)acrylate, and the same applies also to a metal (meth)acrylate or the like.

As a method for producing such a fluorinated compound, a method of taking out the fluorinated compound by distilling a suspension of a metal iodide and the fluorinated compound obtained by reacting the corresponding polyfluoroalkyl iodide with a metal (meth)acrylate in a solvent such as tert-butanol, by means of a distillation apparatus as shown in FIG. 2, or a method of filtering such a suspension and then taking out the fluorinated compound by distillation by means of one distillation apparatus, as shown in FIG. 3, is known (e.g. JP-A-2001-19663).

In either case, a liquid containing a large amount of a solvent was charged into the apparatus, and it was necessary to enlarge the capacity of the apparatus as compared with the distillate amount of the desired fluorinated compound. Accordingly, there was a problem such that excess heating was required, the fluorinated compound was likely to be polymerized in the apparatus, and the formed polymer tended to deposit on the interior of the apparatus. And, due to the deposition of the polymer, the thermal conductivity of the apparatus tended to deteriorate, whereby excess heating would further be required, and polymerization would further proceed, thus leading to such a problem that the distillation yield deteriorated, or removal of the deposited polymer was required. Further, if distillation was carried out under reduced pressure in order to avoid such excess heating, it became difficult to separate the solvent and low boiling point by-products (such as polyfluoroalkylolefins, etc.) formed by the reaction, thus leading to a problem of remarkably deteriorating the efficiency for recovery of the solvent.

It is an object of the present invention to solve the above-mentioned drawbacks of the prior art and to provide a process for producing a polyfluoroalkyl (meth)acrylate, which provides a high yield and which is excellent in the operation efficiency in distillation and purification.

The present invention provides a process for producing a polyfluoroalkyl (meth)acrylate, which comprises isolating, from a reaction mixture containing a polyfluoroalkyl (meth)acrylate obtained by reacting a polyfluoroalkyl iodide of the formula $C_nF_{2n+1}(CH_2)_mI$ (wherein n is an integer of from 2 to 7, and m is an integer of from 1 to 4) with a metal (meth)acrylate in tert-butanol, said polyfluoroalkyl (meth)acrylate by the following steps (1) to (3):

(1) a step of taking out a crude liquid from the reaction mixture by solid-liquid separation;

(2) a step of distilling the crude liquid to separate it into compound group A of compounds having a lower boiling point than the polyfluoroalkyl (meth)acrylate and compound group B of the polyfluoroalkyl (meth)acrylate and compounds having a higher boiling point than the polyfluoroalkyl (meth)acrylate; and (3) a step of distilling and purifying the polyfluoroalkyl (meth)acrylate from the compound group B in the presence of a polymerization inhibitor.

In the accompanying drawings, FIG. 1 is a diagrammatical view showing an example of the apparatus which is useful for carrying out the process of the present invention.

Figure 1:
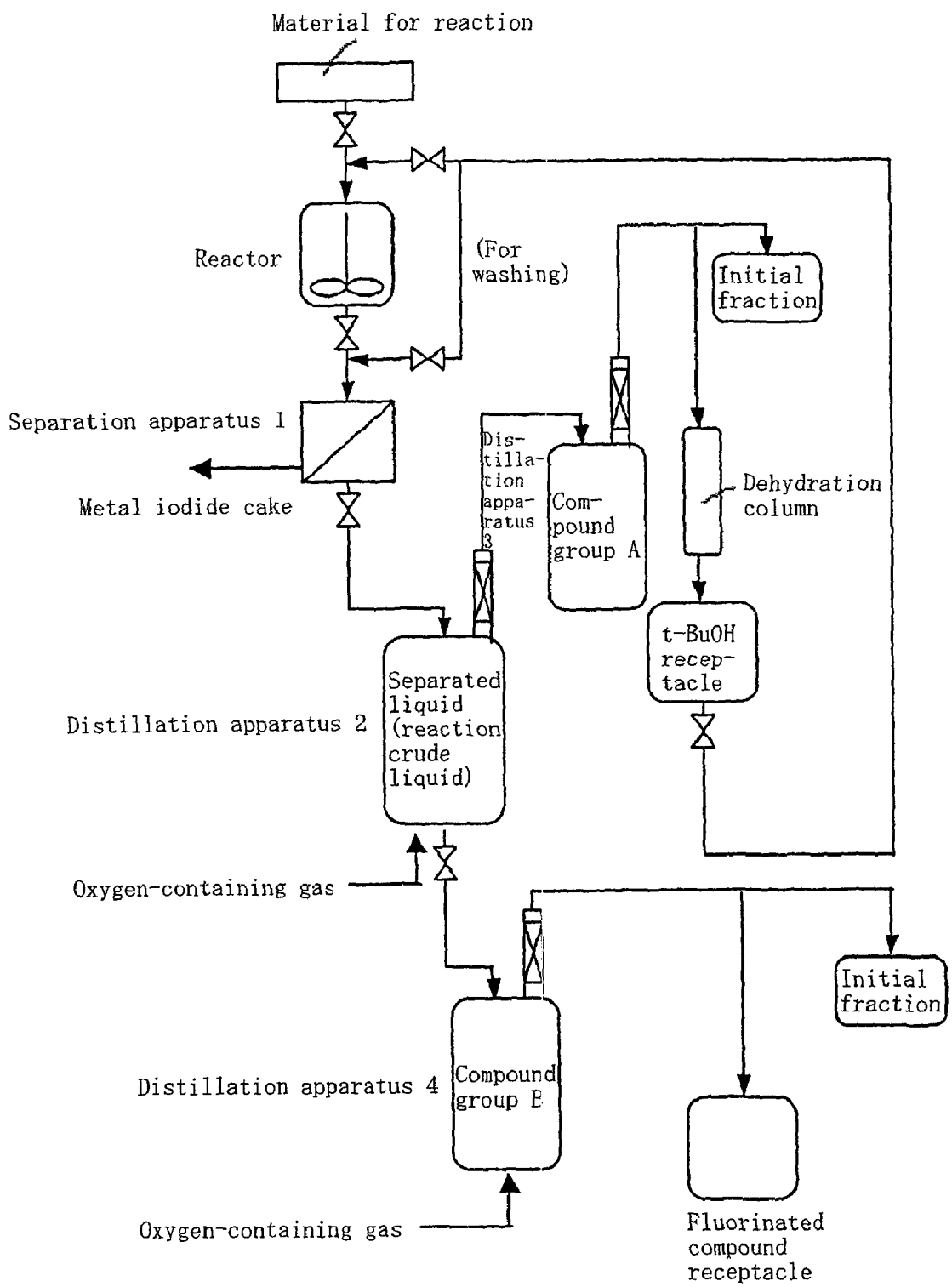
Figure 2:
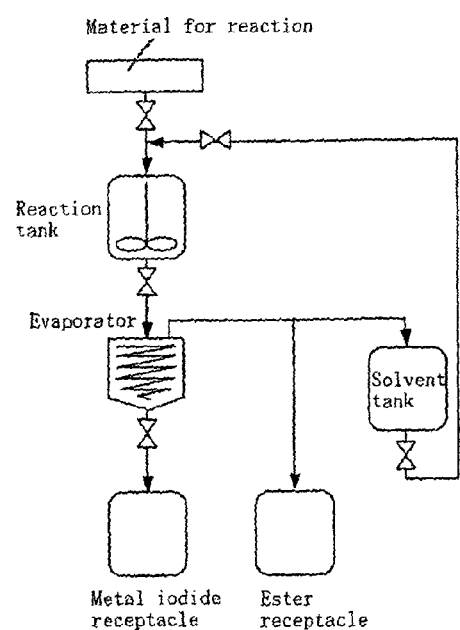
FIG. 2 is a diagrammatical view showing an example of the apparatus which was used for carrying out a conventional process.
Figure 3:
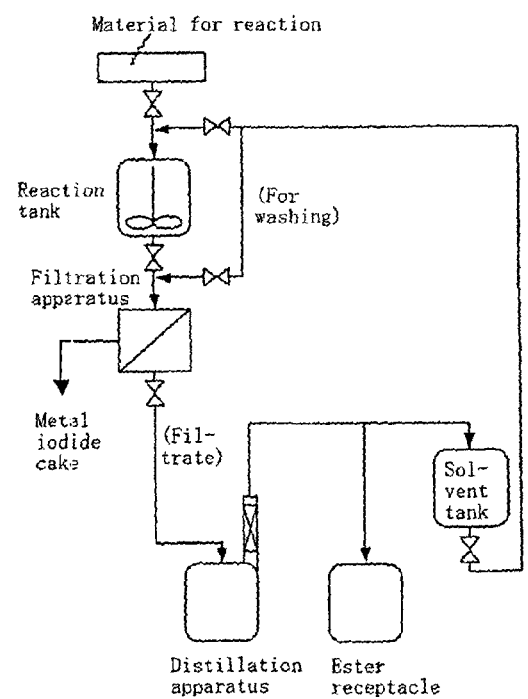
FIG. 3 is a diagrammatical view showing another example of the apparatus which was used for carrying out a conventional process.

Now, the present invention will be described with reference to FIG. 1. However, it should be understood that the process shown in FIG. 1 is an example, and the present invention is by no means limited to FIG. 1.

Production of a Reaction Mixture

Into a reactor, raw material $C_nF_{2n+1}(CH_2)_mI$ (wherein n and m are as defined above), a metal (meth)acrylate and tert-butanol are charged and subjected to an esterification reaction to obtain a reaction mixture containing the fluorinated compound. Such a reaction is preferably conducted in the presence of a polymerization inhibitor.

In $C_nF_{2n+1}(CH_2)_mI$, n is preferably from 4 to 6, more preferably 4 or 6, and m is preferably from 2 to 4, more preferably 2.

Further, the metal (meth)acrylate is preferably a compound of the formula $CH_2=CXCOOM$ (wherein M is a monovalent metal ion, and X is a hydrogen atom or a methyl group). The monovalent metal is preferably an alkali metal or an alkaline earth metal. The metal (meth)acrylate is preferably an alkali metal salt such as a lithium salt, a sodium salt or a potassium salt, particularly preferably a potassium salt.

The above-mentioned tert-butanol is a solvent. As, the polymerization inhibitor, hydroquinone, methoquinone, phenothiazine, cresol, tert-butylcatechol, diphenylamine, a p-phenylene diamine or an N-oxyl compound may, for example, be preferred. Such polymerization inhibitors may be used alone or in combination as a mixture of two or more of them.

The fluorinated compound is preferably a compound of the formula $C_nF_{2n+1}(CH_2)_mOCOCX=CH_2$. Further, by this reaction, a metal iodide will be formed.

In such a reaction, the amount of the metal (meth)acrylate to be used, is preferably from 0.90 to 1.10 mol, more preferably from 0.95 to 1.05 mol, per mol of $C_nF_{2n+1}(CH_2)_mI$. The amount of tert-butanol to be used, is preferably from 4.0 to 10.0 mol, more preferably from 5.0 to 8.0 mol, most preferably from 5.0 to 7.0 mol, per mol of $C_nF_{2n+1}(CH_2)_mI$. When tert-butanol is within such a range, the volume efficiency of the reactor and the conversion will be high. The amount of the polymerization inhibitor is preferably from 0.001 to 0.05 mol, more preferably from 0.01 to 0.03 mol, per mol of the metal (meth)acrylate.

The reaction temperature is preferably from 130 to 220° C., more preferably from 140 to 180° C., most preferably from 145 to 175° C. Within such a temperature range, the conversion will be high, and formation of by-products in the reaction will be suppressed. With respect to the reaction time, the optimum time may suitably be selected depending upon the reaction temperature to be employed, and in the case of from 160 to 180° C., the reaction time is preferably from 4 to 12 hours, more preferably from 6 to 10 hours. Within such a range, the conversion will be high, and formation of by-products in the reaction can be suppressed.

Step (1)

The step of taking out a crude liquid from the reaction mixture containing the fluorinated compound obtained by the reaction, by solid-liquid separation, is carried out by means of a separation apparatus 1. As the method for such solid-liquid separation, a filtration method or a centrifugal separation method is preferred. As a filtration apparatus, a pressure filtration apparatus, a reduced pressure filtration apparatus or a centrifugal separation apparatus, may, for example, be mentioned. As the centrifugal separation machine, a batch type centrifugal separator or a continuous type centrifugal separator may, for example, be mentioned. The separation apparatus is preferably provided with a heater to prevent solidification of tert-butanol. The temperature at the time of the separation is preferably from 20 to 60° C., more preferably from 30 to 40° C., to prevent solidification of tert-butanol and to prevent a polymerization reaction of the fluorinated compound.

The solid phase remained after taking out of the crude liquid, is a metal iodide in the form of a cake. It is preferred to wash the solid phase with tert-butanol and take out the fluorinated compound contained in or attached to the solid phase, whereby the recovery efficiency will be improved. Further, in order to further increase the efficiency for recovery of the fluorinated compound, it is preferred to add a stirrer to the pressure filtration apparatus or the reduced pressure filtration apparatus. It is preferred that the solution containing the fluorinated compound, obtained by such washing is combined with the crude liquid previously obtained and used as combined in the step (2).

Step (2)

The step (2) is carried out by means of a distillation apparatus 2. The distillation apparatus has a heating tank and a distillation column. The crude liquid obtained in the step (1) is introduced into the distillation column, and compound group A of compounds having a lower boiling point than the fluorinated compound is separated as a distillate, and compound group B of the fluorinated compound and compounds having a higher boiling point than the fluorinated compound, is separated as the bottoms. The distillation in the step (2) is preferably a continuous distillation operation.

The compound group A includes a polyfluoroalkyleneolefin of the formula $C_nF_{2n+1}(CH_2)_{m-2}CH=CH_2$ as a by-product in the reaction in a case where m is at least 2, tert-butanol, water, etc.

The above compound group B includes, in addition to the fluorinated compound as the desired product, compounds of the formulae $C_nF_{2n+1}(CH_2)_mOCOCHXCH_2OC(CH_3)_3$, $C_nF_{2n+1}(CH_2)_mOCOCHXCH_2OCOCHX=CH_2$, and $C_nF_{2n+1}(CH_2)_mOCOCHXCH_2O(CH_2)_mC_nF_{2n+1}$ (wherein n, m and X are as defined above).

The distillation operation in the step (2) may be carried out under atmospheric pressure or under reduced pressure. To prevent polymerization of the fluorinated compound in the heating tank, it is preferred to carry out the distillation at a temperature as low as possible, and distillation under reduced pressure is preferred. Compound group A has a boiling point of at most about 100° C. under atmospheric pressure, and in order to take out compound group A as a distillate, the degree of reduced pressure is preferably from $6.67 \times 10^3$ to $66.7 \times 10^3$ Pa (from 50 to 500 mmHg), more preferably from $26.7 \times 10^3$ to $40.0 \times 10^3$ Pa (from 200 to 300 mmHg).

In the step (2), in order to prevent a polymerization reaction of the fluorinated compound in the distillation column and the heating tank, it is preferred to carry out the distillation in an atmosphere containing oxygen gas. The oxygen gas is usually diluted and supplied as an oxygen-containing gas. The supply location is not particularly limited and is preferably in the heating tank in the case of a batch type distillation operation, and preferably at the lowest portion of the distillation column in the case of a continuous distillation operation. Further, the supply location is preferably more than one.

The content of the oxygen gas in the oxygen-containing gas to be supplied as described above, is preferably from 0.01 to 5%, more preferably from 0.02 to 3%, based on the amount of vapor (by volume calculated as in the standard state) generated in the heating tank. Within such a range, the effect for preventing the polymerization reaction is sufficient, and the increase in the amount of vapor to be carried by the oxygen-containing gas is small, and in a case where the distillation is carried out under reduced pressure, the load to the vacuuming apparatus is little.

The step (2) is preferably conducted in the presence of a polymerization inhibitor to prevent the polymerization reaction of the fluorinated compound. Such a polymerization inhibitor may be one added during the reaction, which still remains, or may be added afresh in the step (2). Such a polymerization inhibitor is preferably the same compound as the above-mentioned polymerization inhibitor, and the amount thereof is preferably from 0.001 to 0.05 mol, more preferably from 0.01 to 0.03 mol, per mol of the fluorinated compound.

Step (3)

The step (3) is carried out by means of a distillation apparatus 4 in such a manner that the compound group B obtained in the step (2) is introduced into a distillation column, and the fluorinated compound is taken out as a distillate from the distillation column.

The distillation operation in the step (3) may be carried out under atmospheric pressure or under reduced pressure. In order to prevent the polymerization reaction of the fluorinated compound in the heating tank, it is preferred to carry out the distillation at a temperature as low as possible, and distillation under reduced pressure is preferred. The compound group B has a boiling point of at least about 150° C. under atmospheric pressure (for example, the boiling point of $C_6F_{13}(CH_2)_2OCOC(CH_3)=CH_2$ is about 230° C. under atmospheric pressure), and in order to take out the fluorinated compound as a distillate, the pressure is preferably from $0.13 \times 10^3$ to $3.33 \times 10^3$ Pa (from 1 to 25 mmHg), more preferably from $0.13 \times 10^3 \times 1.33 \times 10^3$ Pa (from 1 to 10 mmHg).

In the step (3), it is preferred to carry out the distillation in an atmosphere containing oxygen gas in order to prevent the polymerization reaction of the fluorinated compound. The oxygen gas is usually diluted and supplied as an oxygen-containing gas. The supply location is not particularly limited and is preferably in the heating tank. The supply location is preferably more than one.

The content of the oxygen gas in the oxygen-containing gas to be supplied as described above, is preferably from 0.01 to 5%, more preferably from 0.02 to 3%, based on the amount of vapor (by volume calculated as in the standard state) generated in the heating tank. Within such a range, the effect for preventing the polymerization reaction is sufficient, the increase of the amount of vapor to be carried by the oxygen-containing gas is small, and when distillation is carried out under reduced pressure, the load to the vacuuming apparatus is little.

The step (3) is carried out in the presence of a polymerization inhibitor in order to prevent the polymerization reaction of the fluorinated compound. Such a polymerization inhibitor may be one added during the reaction or in the step (2), which still remains, or may be added afresh in the step (3). The polymerization inhibitor is preferably the same compound as the above-mentioned polymerization inhibitor, and the amount thereof is preferably from 0.001 to 0.05 mol, more preferably from 0.01 to 0.03 mol, per mol of the fluorinated compound.

Step (4)

In the present invention, it is preferred to further add step (4) of distilling the compound group A obtained in the step (2) and taking out tert-butanol as a distillate from the distillation column. Such a step can be carried out by means of a distillation apparatus 3.

The distillation operation in the step (4) may be carried out under atmospheric pressure or under reduced pressure. In order to increase the efficiency for recovery of tert-butanol, it is preferred to carry out the distillation under atmospheric pressure or under slightly reduced pressure.

A perfluoroalkylolefin contained in the compound group A may sometimes form an azeotropic mixture with tert-butanol depending upon the carbon number of its perfluoroalkyl group ($C_nF_{2n+1}$). For example, in a case where the perfluoroalkylolefin is $C_6F_{13}CH=CH_2$ (boiling point: 106° C./1.01×$10^6$ Pa), it forms an azeotropic mixture of about 60 mass % (boiling point: about 78° C./1.01×$10^6$ Pa) with tert-butanol (boiling point: 82.5° C./1.01×$10^6$ Pa).

In the step (4), it is possible to recover tert-butanol obtaining substantially no water. Water contained in a very small amount in the compound group A is mainly one included during the separation operation in the step (1) or during the transfer operation of the separated liquid. Water forms a 22% azeotropic mixture (boiling point: 80° C./1.01×$10^6$ Pa) with tert-butanol. Accordingly, water present in a very small amount in the compound group A may be azeotropically boiled with tert-butanol and can be removed as an initial distillate at the initial stage of the step. The recovered tert-butanol is preferably utilized as a solvent for the reaction or for washing the solid phase after the separation operation in the step (1).

Further, a polyfluoroalkylolefin such as $C_6F_{13}CH=CH_2$ taken out as a distillate in the step (4) can be converted to a polyfluoroalkyl alcohol such as $C_6F_{13}CH_2CH_2CH_2OH$ by a reaction with methanol or ethanol in the presence of a radical initiator. Further, such a polyfluoroalkyl alcohol may be led to a fluorinated compound by an esterification reaction with (meth)acrylic acid, whereby the selectivity and the yield of the reaction can be improved.

Now, the present invention will be described with reference to Reaction Examples (Examples 1 to 8), Working Examples (Examples 10 to 13 and 16), Comparative Examples (Examples 14, 15, 17 and 18) and Reference Examples (Examples 9 and 19), but it should be understood that the present invention is by no means restricted by such Examples. Further, the gas chromatography analysis was carried out by means of 6850 gas chromatograph system manufactured by Agilent Technologies Inc. (capillary column for analysis: DB1301 (30.0 m-0.25 mm-1.0 μm)). Further, measurement of the fluorine content was carried out by means of a combustion-pyrohydrolysis method.

EXAMPLES 1 TO 5

Reaction Step

Into a pressure resistant autoclave (10 liters) equipped with stirring vanes (Full Zone, manufactured by SHINKO PANTEC CO., LTD.), $C_qF_{2q+1}(CH_2)_2I$ (wherein q is 4 or 6, hereinafter referred to as FI), potassium (meth)acrylate, phenothiazine (hereinafter referred to as PTZ) and tert-butanol (hereinafter referred to also as BuOH) were charged in the amounts (unit: mol) as shown in Table 1, and an ester-forming reaction was carried out under the reaction conditions shown in Table 1 to obtain a reaction mixture. The conversion and selectivity of the reaction are shown in Table 1.

EXAMPLES 6 TO 9

Reaction Step

Into a pressure resistant autoclave (0.5 liter) equipped with stirring vanes (disk turbine), FI, potassium (meth)acrylate, PTZ and BuOH were charged in the amounts (unit: mol) as shown in Table 1, and an ester-forming reaction was carried out under the reaction conditions shown in Table 1 to obtain a reaction mixture. The conversion and selectivity of the reaction are shown in Table 1.

Further, the abbreviations in Table 1 have the following meanings.

MAK: Potassium methacrylate,
AK: Potassium acrylate,
FA: $C_qF_{2q+1}C_2H_4OCOCH=CH_2$,
FMA: $C_qF_{2q+1}C_2H_4OCOCCH_3=CH_2$,
OLF: $C_qF_{2q+1}CH=CH_2$,
AL: $C_qF_{2q+1}C_2H_4OH$.

TABLE 1

| Ex. | FI | MAK or AK | PTZ | BuOH | Reaction temperature [° C.] | Reaction time [hr] | Conversion [%] | Selectivity [%] FA or FMA | OLF | AL |
|---|---|---|---|---|---|---|---|---|---|---|
| 1 | q = 6 8.2 | MAK 8.6 | 0.17 | 43.3 | 170 | 6 | 99.0 | FMA 88.0 | 11.4 | 0.6 |
| 2 | q = 6 6.7 | MAK 7.0 | 0.14 | 53.0 | 160 | 9 | 99.0 | FMA 88.4 | 11.1 | 0.5 |
| 3 | q = 6 8.2 | MAK 8.6 | 0.17 | 43.3 | 160 | 9 | 96.7 | FMA 89.5 | 10.1 | 0.4 |
| 4 | q = 6 8.1 | MAK 8.1 | 0.17 | 41.1 | 160 | 9 | 93.2 | FMA 89.2 | 10.8 | 0 |
| 5 | q = 4 10.3 | AK 10.3 | 0.21 | 52.3 | 150 | 6 | 90.5 | FA 86.5 | 13.5 | 0 |
| 6 | q = 4 0.38 | AK 0.39 | 0.01 | 1.93 | 160 | 6 | 93.4 | FA 87.4 | 12.1 | 0.5 |
| 7 | q = 6 0.39 | MAK 0.39 | 0.01 | 2.00 | 130 | 6 | 32.7 | FMA 90.6 | 9.1 | 0.3 |

TABLE 1-continued

| Ex. | MAK or FI AK | PTZ | BuOH | Reaction temperature [°C.] | Reaction time [hr] | Conversion [%] | Selectivity [%] FA or FMA | OLF | AL |
|---|---|---|---|---|---|---|---|---|---|
| 8 | q = 6 MAK 0.30 0.30 | 0.01 | 1.90 | 160 | 9 | 78.0 | FMA 76.9 | 23.1 | 0 |
| 9 | q = 4 AK 1.27 0.25 | 0.03 | 0 | 150 | 6 | 0.03 | FA 74.3 | 25.7 | 0 |

EXAMPLE 10

Separation Step

The reaction mixture containing $C_6F_{13}(CH_2)_2OCOC(CH_3)=CH_2$ and potassium iodide, obtained in Example 1, was subjected to solid-liquid separation under the conditions as shown in Table 2 by means of a pressure filtration apparatus (1.5 liters, manufactured by ADVANTEC TOYO KAISHA, LTD.). The solid phase containing potassium iodide was washed a few times by means of tert-butanol with stirring and then dried under reduced pressure, whereupon the fluorine content in the solid phase was measured. The tert-butanol solution used for washing the solid phase and the liquid phase (the filtrate) were put together to obtain a crude liquid. The results are shown in Table 2.

EXAMPLE 11

Separation Step

Solid-liquid separation was carried out under the conditions as shown in Table 2 by means of a centrifugal filtration apparatus provided with a jacket (manufactured by Sanyo Rikagaku Kiki K.K.) instead of the pressure filtration apparatus in Example 10. The solid phase was washed a few times by means of tert-butanol and then dried under reduced pressure, whereupon the fluorine content in the solid phase was measured. The tert-butanol solution used for washing the solid phase and the liquid phase were put together to obtain a crude liquid. The results are shown in table 2.

EXAMPLE 12

Separation Step

Solid-liquid separation was carried out under the conditions shown in Table 2 by means of a reduced pressure filtration apparatus provided with a jacket (1.5 liters, manufactured by ADVANTEC TOYO KAISHA, LTD.) instead of the pressure filtration apparatus in Example 10. The solid phase was washed a few times with tert-butanol with stirring and then dried under reduced pressure, whereupon the fluorine content in the solid phase was measured. The tert-butanol solution used for washing the solid phase and the liquid phase were put together to obtain a crude liquid. The results are shown in Table 2.

EXAMPLE 13

Separation Step

Solid-liquid separation was carried out under the conditions shown in Table 2 by means of a centrifugal separator (cooled high speed centrifugal separator H-9R, manufactured by KOKUSAN Corporation) instead of the pressure filtration apparatus in Example 10. The liquid phase was obtained by decantation, and then, to wash the solid phase, tert-butanol was put and stirred, whereupon centrifugal separation and decantation were carried out again. The obtained liquid phases were put together to obtain a crude liquid. The washed solid phase was dried under reduced pressure, whereupon the fluorine content contained in the solid phase was measured. The results are shown in Table 2.

EXAMPLE 14

Separation Step

The reaction mixture obtained in Example 1 was put in an autoclave (10 liters) equipped with double helical vanes and heated under atmospheric pressure to 120° C., whereby tert-butanol and $C_6F_{13}CH=CH_2$ (boiling point: 106° C./1.01×$10^6$ Pa) were recovered. Then, the pressure was stepwisely lowered to about $1.3×10^3$ Pa (10 mmHg), and the temperature was raised to 160° C. with stirring to evaporate a liquid component. The fluorine content in the solid phase remaining in the autoclave was measured. The results are shown in Table 2.

EXAMPLE 15

Separation Step

The operation was the same as in Example 14 except that in Example 14, the reaction mixture of Example 2 was used instead of the reaction mixture of Example 1, and the temperature was raised to 190° C. instead of 160° C. The results are shown in Table 2.

TABLE 2

| Ex. | Separation method | Temp. [°C.] | Particle diameter on the filter material [µm] | Rotational speed [rpm] | Solid phase appearance | Fluorine content [ppm] |
|---|---|---|---|---|---|---|
| 10 | Pressure filtration | 30 | 4 | — | White | 100 |
| 11 | Centrifugal filtration | 30 | 4 | 1000 | White | 180 |
| 12 | Reduced pressure filtration | 30 | 4 | — | White | 100 |
| 13 | Centrifugal separation | 30 | — | 2000 | White | 250 |
| 14 | Evaporation to dryness | 160 | — | — | Brown | 1900 |
| 15 | Evaporation to dryness | 190 | — | — | Black | 40500 |

EXAMPLE 16

Distillation Step

Into a glass container (10 liters) having a heating device and equipped with a distillation column (inner diameter: 35 mm, height: 600 mm) having a theoretical plate number of 30 plates, 10.0 kg of the crude liquid containing 4034 g of $C_6F_{13}(CH_2)_2OCOC(CH_3)=CH_2$ obtained in Example 10, and 20 g of phenothiazine, were charged, and distillation was carried out (pressure: $13.3 \times 10^3$ to $40.0 \times 10^3$ Pa, temperature: 80 to 90° C.) while introducing air from the bottom of the glass container so that oxygen would be 3% by volume based on the amount of vapor generated in the glass container. From the column top, 5426 g of a distillate composed mainly of tert-butanol was obtained, and from the column bottom, 4422 g of the bottom composed mainly of $C_6F_{13}(CH_2)_2OCOC(CH_3)=CH_2$ was obtained.

5426 g of the obtained distillate was charged into a glass container (10 liters) having a heating device, equipped with a distillation column (inner diameter: 35 mm, height: 600 mm) having a theoretical plate number of 30 plates, and distillation was carried out under atmospheric pressure. 759 g of an azeotropic mixture of tert-butanol and $C_6F_{13}CH=CH_2$, etc. was obtained as the initial fraction, and 4598 g of tert-butanol having a purity of 99.5%, was obtained as a distillate. The recovery rate of tert-butanol from the crude liquid obtained in Example 10 was 90.3%.

Further, 4422 g of the obtained bottom was charged into a glass container (5 liters) having a heating device equipped with a distillation column (inner diameter: 35 mm, height: 600 mm) having a theoretical plate number of 30 plates, and distillation was carried out (pressure: $13.3 \times 10^3$ Pa, temperature: 100 to 130° C., while introducing air from the bottom of the glass container so that the volume of oxygen would be 3%, based on the amount of vapor generated in the glass container. 3538 g of $C_6F_{13}(CH_2)_2OCOC(CH_3)=CH_2$ having a purity of 99.5% was obtained as a distillate. The distillation yield of $C_6F_{13}(CH_2)_2OCOC(CH_3)=CH_2$ from the crude liquid obtained in Example 10, was 87.7%. The distillation residue was 300 g, the main components of the residue were $C_6F_{13}(CH_2)_2OCOC(CH_3)=CH_2$ and phenothiazine, and no polymer was formed.

EXAMPLE 17

Distillation Step 9600 g of the crude liquid containing 3873 g of $C_6F_{13}(CH_2)_2OCOC(CH_3)=CH_2$, obtained in Example 10 was charged into a glass container (10 liters) having a heating device, equipped with a distillation column (inner diameter: 35 mm, height: 600 mm) having a theoretical plate number of 30 plates, and distillation was carried out under atmospheric pressure. 720 g containing an azeotropic mixture of tert-butanol and $C_6F_{13}CH=CH_2$, was obtained as an initial fraction, and 4410 g of tert-butanol having a purity of 99.5%, was obtained as a distillate. The recovery rate of tert-butanol from the crude liquid obtained in Example 10 was 90.2%.

Then, the pressure was stepwise lowered to $1.33 \times 10^3$ Pa (10 mmHg), and the temperature in the glass container was raised to 130° C., whereby 2327 g of $C_6F_{13}(CH_2)_2OCOC(CH_3)=CH_2$ having a purity of 99.5% was obtained as a distillate. The distillation yield of $C_6F_{13}(CH_2)_2OCOC(CH_3)=CH_2$ from the crude liquid obtained in Example 10 was 57.4%. The distillation residue was 1150 g, and a viscous polymer was contained in the residue.

EXAMPLE 18

Distillation Step 10.0 kg of the crude liquid containing 4022 g of $C_6F_{13}(CH_2)_2OCOC(CH_3)=CH_2$ obtained in Example 10 was charged into a glass container (10 liters) having a heating device, equipped with a distillation column (inner diameter: 35 mm, height: 600 mm) having a theoretical plate number of 30 plates, and distillation was carried out (pressure: $13.3 \times 10^3$ to $40.0 \times 10^3$ Pa, temperature: 80 to 90° C.). 5442 g of a distillate containing tert-butanol as the main component and 4402 g of the bottom containing $C_6F_{13}(CH_2)_2OCOC(CH_3)=CH_2$ as the main component, were obtained. 5442 g of the obtained distillate was charged into a glass container (10 liters) having a heating device, equipped with a distillation column (inner diameter: 35 mm, height: 600 mm) having a theoretical plate number of 30 plates, and distillation was carried out under atmospheric pressure. 740 g containing an azeotropic mixture of tert-butanol and $C_6F_{13}CH=CH_2$ was obtained as an initial fraction, and 4623 g of tert-butanol having a purity of 99.5%, was obtained as a distillate. The recovery rate of tert-butanol from the crude liquid obtained in Example 10 was 90.5%.

Further, 4402 g of the obtained bottom was charged into a glass container (5 liters) having a heating device, equipped with a distillation column (inner diameter: 35 mm, height: 600 mm) having a theoretical plate number of 30 plates, and distillation was carried out (pressure: $1.33 \times 10^3$ Pa (10 mmHg), temperature: 100 to 130° C.). 2896 g of $C_6F_{13}(CH_2)_2OCOC(CH_3)=CH_2$ having a purity of 99.5% was obtained as a distillate. The distillation yield of $C_6F_{13}(CH_2)_2OCOC(CH_3)=CH_2$ from the crude liquid obtained in Example 10, was 72.0%. The distillation residue was 800 g, and a viscous polymer was contained in the residue.

EXAMPLE 19

Reference Reaction 500 mL of water was added to the azeotropic mixture of tert-butanol and $C_6F_{13}CH=CH_2$, obtained in Example 16, followed by stirring for a few minutes, and then, 500 mL of water was added, followed by stirring. Then, the mixture was left to stand still for phase separation. As the lower phase portion, 400 g of $C_6F_{13}CH=CH_2$ having a purity of 99.2% was obtained. 740 g of methanol was put into a pressure resistant autoclave (2.5 liters) equipped with a stirring vanes (Full Zone, manufactured by SHINKO PANTEC CO., LTD.) and heated, and when the temperature reached 120° C., a mixed solution of 400 g of $C_6F_{13}CH=CH_2$ and 2.5 g of a radical initiator "Perbutyl D" (manufactured by NOF Corporation), was added in an amount of 2 g every minutes to carry out an alcohol-forming reaction.

After confirming disappearance of $C_6F_{13}CH=CH_2$ by gas chromatography, the reaction was terminated by cooling to obtain a reaction liquid. From the obtained reaction liquid, majority of methanol was distilled off under reduced pressure, and then, the reaction liquid was washed with water to remove the remaining methanol thereby to obtain 430 g of $C_6F_{13}CH_2CH_2CH_2OH$ having a purity of 92.8%.

Into a glass container (1 liter) equipped with stirring vanes, 430 g of the obtained $C_6F_{13}CH_2CH_2CH_2OH$, 100 g of methacrylic acid, 22 g of p-toluene sulfonic acid monohydrate (hereinafter referred to as PTSA) and 1.3 g of hydroquinone were put, the temperature was brought to 80° C., and an esterification reaction was carried out under reduced pressure ($4.0\times10^3$ to $40.0\times10^3$ Pa) to obtain a reaction liquid. The obtained reaction liquid was subjected to filtration and washed with water to obtain a crude product.

The obtained crude product and 2 g of hydroquinone were put into a glass container (1 liter) having a heating device, equipped with a distillation column (inner diameter: 35 mm, height: 600 mm) having a theoretical plate number of 30 plates, and distillation was carried out (pressure: $1.33\times10^3$ Pa (10 mmHg), temperature: 110 to 140° C.) while introducing air from the bottom of the glass container so that oxygen would be 3 volume % based on the amount of vapor generated in the glass container. 402 g of $C_6F_{13}(CH_2)_3OCOC(CH_3)=CH_2$ having a purity of 99.5%, was obtained as a distillate.

According to the process of the present invention, a fluorinated compound having a high purity can be obtained in good yield. According to the process of the present invention, the recovery rate of tert-butanol as the solvent, can be made high, no polymerization reaction of the fluorinated compound will take place, and the fluorine content in the recovered metal iodide is little, whereby iodine can readily be recovered from the metal iodide.

According to the process of the present invention, the polymerization reaction of the fluorinated compound can be prevented, the number of removal operations can be reduced since the polymer formed in the distillation column is little, and the process is excellent in the purification operation efficiency of the fluorinated compound and excellent in the productivity.

The entire disclosure of Japanese Patent Application No. 2003-160885 filed on Jun. 5, 2003 including specification, claims, drawings and summary is incorporated herein by reference in its entirety.

What is claimed is:

1. A process for producing a polyfluoroalkyl (meth)acrylate, which comprises isolating, from a reaction mixture containing a polyfluoroalkyl (meth)acrylate obtained by reacting a polyfluoroalkyl iodide of the formula $C_nF_{2n+1}(CH_2)_mI$ (wherein n is an integer of from 2 to 7, and m is an integer of from 1 to 4) with a metal (meth)acrylate in tert-butanol, said polyfluoroalkyl (meth)acrylate by the following steps (1) to (3):
   (1) taking out a crude liquid from the reaction mixture by solid-liquid separation;
   (2) distilling the crude liquid in an atmosphere comprising oxygen gas to separate it into compound group A of compounds having a lower boiling point than the polyfluoroalkyl (meth)acrylate and compound group B of the polyfluoroalkyl (meth)acrylate and compounds having a higher boiling point than the polyfluoroalkyl (meth)acrylate; and
   (3) distilling and purifying the polyfluoroalkyl (meth)acrylate from the compound group B in the presence of a polymerization inhibitor, wherein said step (3) is carried out in an oxygen-containing atmosphere comprising oxygen gas, wherein the oxygen gas is present in the oxygen-containing gas in an amount of from 0.01 to 5%, based on the amount of vapor by volume calculated as in the standard state generated in a heating tank.

2. The process according to claim 1, wherein the separation method in the step (1) is a filtration method or a centrifugal separation method.

3. The process according to claim 1, wherein said reaction and/or the step (2) is carried out in the presence of a polymerization inhibitor.

4. The process according to claim 1, wherein the polymerization inhibitor is hydroquinone, methoquinone, phenothiazine, cresol, tert-butyl catechol, diphenylamine, a p-phenylenediamine or an N-oxyl compound.

5. The process according to claim 1, wherein the metal (meth)acrylate is a lithium salt, a sodium salt or a potassium salt.

6. The process according to claim 1, wherein the temperature in the step (1) is from 20 to 60° C.

7. The process according to claim 1, wherein the pressure in the step (2) is from $6.67\times10^3$ to $66.7\times10^3$ Pa (from 50 to 500 mmHg).

8. The process according to claim 1, wherein the pressure in the step (3) is from $0.13\times10^3$ to $3.33\times10^3$ Pa (from 1 to 25 mmHg).

9. The process according to claim 1, wherein the content of the oxygen gas in the oxygen-containing gas in the step (2) is from 0.01 to 5%, based on the amount of vapor (by volume calculated as in the standard state) generated in a heating tank.

10. The process according to claim 1, wherein n is from 4 to 6, and m is from 2 to 4.

11. The process according to claim 10, wherein n is 4 or 6, and m is 2.

12. The process according to claim 5, wherein the metal (meth)acrylate is a potassium salt.

13. The process according to claim 6, wherein the temperature in the step (1) is from 30 to 40° C.

14. The process according to claim 1, wherein the solid phase remaining after taking out the crude liquid in the step (1) is washed with tert-butanol, whereby a solution comprising polyfluoroalkyl (meth)acrylate is obtained, and said solution is combined with said crude liquid and used as combined in the step (2).

15. The process according to claim 1, additionally comprising, after step (3), a step (4) which comprises distilling the compound group A obtained in the step (2) and taking out tert-butanol as a distillate from a distillation column.

16. The process according to claim 15, wherein in step (4), tert-butanol is recovered with substantially no water.

17. The process according to claim 15, additionally comprising converting a polyfluoroalkyl olefin taken out as a distillate in the step (4) to a polyfluoroalkyl alcohol by reaction with methanol or ethanol in the presence of a radical initiator.

18. The process according to claim 17, additionally comprising esterifying the polyfluoroalkyl alcohol with (meth)acrylic acid.

19. The process according to claim 1, wherein the amount is from 0.02 to 3%.

* * * * *